United States Patent
Mahe et al.

(10) Patent No.: US 6,653,317 B2
(45) Date of Patent: Nov. 25, 2003

(54) PYRIMIDINE 3-OXIDE COMPOUNDS FOR INDUCING/STIMULATING HAIR GROWTH AND/OR RETARDING HAIR LOSS

(75) Inventors: Yann Mahe, Morsang sur Orge (FR); Jean-François Michelet, Creteil (FR); Patrick Pichaud, Velizy (FR); Jean-Baptiste Galey, Aulnay-Sous-Bois (FR)

(73) Assignee: Societe l'Oreal S.A., Paris (FR)

( * ) Notice: Subject to any disclaimer, the term of this patent is extended or adjusted under 35 U.S.C. 154(b) by 0 days.

(21) Appl. No.: 10/301,733

(22) Filed: Nov. 22, 2002

(65) Prior Publication Data

US 2003/0130294 A1 Jul. 10, 2003

Related U.S. Application Data

(62) Division of application No. 09/874,053, filed on Jun. 6, 2001, now Pat. No. 6,511,659, which is a division of application No. 09/360,495, filed on Jul. 23, 1999, now Pat. No. 6,291,468.

(30) Foreign Application Priority Data

Jul. 24, 1998 (FR) .............................. 98 09509

(51) Int. Cl.$^7$ .................. C07D 239/48; A61K 7/06; A61K 31/505; A61P 17/14
(52) U.S. Cl. ............. 514/272; 514/275; 514/DIG. 880; 544/320; 544/323; 424/70; 424/443; 424/450
(58) Field of Search ................. 544/320, 323; 514/275, 272, 880, DIG. 880; 424/70, 450, 443

(56) References Cited

U.S. PATENT DOCUMENTS

| | | | |
|---|---|---|---|
| 4,780,537 A | 10/1988 | Vedres et al. | |
| 5,328,914 A | 7/1994 | Hocquaux et al. | |
| 5,466,694 A | 11/1995 | Terranova et al. | |
| 5,610,302 A | 3/1997 | Dufetel et al. | |

FOREIGN PATENT DOCUMENTS

EP 0522964 A 1/1993

OTHER PUBLICATIONS

Paquette, L.A., "Encyclopedia of Reagents for Organic Synthetis", vol. 4, pp. 2742–2743, published by John Wiley & Sons, New York (1995).

*Primary Examiner*—Richard L. Raymond
*Assistant Examiner*—Venkataraman Balasubramanian
(74) *Attorney, Agent, or Firm*—Burns, Doane, Swecker & Mathis, L.L.P.

(57) ABSTRACT

Hair growth-/hair loss-affecting cosmetic/therapeutic compositions contain an effective amount of at least one 2-amino-4-alkylaminopyrimidine 3-oxide having the structural formula (I):

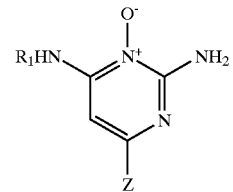

in which $R_1$ is an alkyl radical having from 5 to 20 carbon atoms, and Z is either a hydrogen atom or a radical $-OR_2$, wherein $R_2$ is an alkyl radical having from 1 to 12 carbon atoms, or an acyl derivative or acid addition salt thereof.

18 Claims, No Drawings

PYRIMIDINE 3-OXIDE COMPOUNDS FOR INDUCING/STIMULATING HAIR GROWTH AND/OR RETARDING HAIR LOSS

CROSS-REFERENCE TO RELATED APPLICATIONS

This application is a divisional of copending Application No. 09/874,053, filed Jun. 6, 2001, now U.S. Pat. No. 6,511,659, incorporated by reference herein, which is a divisional of Application No. 09/360,495, filed Jul. 23, 1999, now U.S. Pat. No. 6,291,468.

CROSS-REFERENCE TO PRIORITY APPLICATION

This application claims priority under 35 U.S.C. §119 OF FR-98/09509, filed Jul. 24, 1998, assigned to the assignee hereof and hereby expressly incorporated by reference.

BACKGROUND OF THE INVENTION

1. Technical Field of the Invention

The present invention relates to novel 2-amino-4-alkylaminopyrimidine 3-oxide chemical compounds, to compositions comprised thereof and to the use of such novel compounds/compositions as active principles for inducing and/or stimulating hair growth and/or for preventing hair loss.

2. Description of the Prior Art

In human subjects the growth and renewal of the hair are principally determined by the activity of the hair follicles. This activity is cyclic and essentially entails three phases, i.e., the anagenic phase, the catagenic phase and the telogenic phase.

The active anergenic phase, or growth phase, which lasts for several years and during which the hair elongates, is followed by a very short and transient catagenic phase which lasts for a few weeks, and then a rest or quiescent phase, designated the telogenic phase, which lasts for a few months.

At the end of the rest period, the hair falls out and another cycle begins anew. The head of hair is thus under constant renewal, and out of the approximately 150,000 hairs on a head of hair, at any given instant approximately 10% are at rest and will thus be replaced within a few months.

However, different causes can lead to a considerable, temporary or permanent, loss of hair. Alopecia is essentially due to a disruption in hair renewal which occasions, in a first stage, an acceleration of the frequency of the cycles, at the expense of the quality of the hair and then at the expense of its quantity. A gradual depletion of the head of hair takes place by regression of the so-called "terminal" hairs at the downy stage. Certain regions are preferentially affected, in particular the temples or frontal bulbs in men, and in women, diffuse alopecia of the vertex is observed.

By the term "alopecia" are intended the entire family of afflictions of the hair follicle, the final consequence of which is the partial or general permanent loss of the hair. In a large number of cases, early loss of the hair arises in genetically predisposed individuals and especially affects men. This more particularly applies to androgenetic or androgenic or even androgeno-genetic alopecia.

Active substrates for suppressing or reducing alopecia, and in particular for inducing or stimulating hair growth or reducing hair loss, have long been considered desiderata in the cosmetics and pharmaceutical industries.

In this respect, a large number of very diverse active compounds have already been suggested for such purposes, for example, 2,4-diamino-6-piperidino-pyrimidine 3-oxide or "Minoxidil" described in U.S. Pat. Nos. 4,139,619 and 4,596,812, or the many derivatives thereof, such as those described, for example, in EP-0,353,123, EP-0,356,271, EP-0,408,442, EP-0,522,964, EP-0,420,707, EP-0,459,890 and EP-0,519,819.

Nonetheless, serious need continues to exist for yet other active agents/species potentially more active and/or less toxic than those active substrates to date characterizing the state of this art.

SUMMARY OF THE INVENTION

Accordingly, a major object of the present invention is the provision of novel 2-amino-4-alkylaminopyrimidine 3-oxide compounds having the structural formula (I):

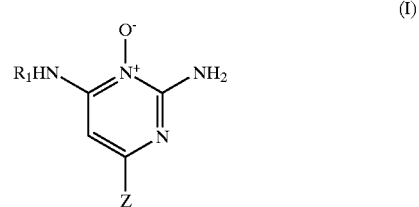

in which $R_1$ is an alkyl radical having from 5 to 20 carbon atoms, and Z is either a hydrogen atom or a radical $-OR_2$, wherein $R_2$ is an alkyl radical having from 1 to 12 carbon atoms, as well as the acyl derivatives or acid addition salts thereof.

The subject compounds are well suited as active principles for inducing and/or stimulating hair growth and/or preventing hair loss.

DETAILED DESCRIPTION OF BEST MODE AND SPECIFIC/PREFERRED EMBODIMENTS OF THE INVENTION

More particularly according to the present invention, it is known to this art that certain polyunsaturated fatty acids, in particular those having 20 carbon atoms, such as arachidonic acid, dihomo-γ-linolenic acid and eicosapentaenoic acid, can be converted in vivo, under the influence of certain specific enzymes contained in living cells, in particular epithelial cells, into certain yet other compounds of eicosanoid type which are useful to the body.

Thus, it is known to this art that the enzymes designated cyclooxygenated generate, from the different fatty acids indicated above, particularly from arachidonic acid, eicosanoids of prostaglandin and thromboxane type, and that the enzymes deemed lipoxygenases are responsible for the formation of eicosanoids of leukotriene type and other hydroxylated acyclic acids containing 20 carbon atoms. Depending on the nature of the enzyme with which it reacts first, the same given polyunsaturated fatty acid (or substrate) may be responsible for the formation of several different metabolites, namely, for example, prostaglandins and leukotrienes.

Cyclooxygenase activity can be defined as the enzymatic activity which converts certain polyunsaturated fatty acids into cyclized oxygenated compounds which are, indeed, highly unstable endoperoxides which thereafter enter the subsequent metabolic pathways.

Prostaglandin-endoperoxide synthase, or cyclooxygenase (or PGHS, EC 1.14.99.1), which is a haemoprotein, is an example of these enzymes exhibiting such activity. It is involved in one of the metabolic pathways of prostaglandins.

It too is known that the enzymatic transformations indicated above and the various reaction products resulting therefrom exert an appreciable influence on the mechanisms of growth of body and/or head hair.

In this respect, it has now been shown that by promoting one or other of the two enzymatic pathways, cyclooxygenated or lipoxygenated, in skin and/or scalp cells, it is possible to substantially modify the growth of body and/or head hair. Compare EP-94/402,055, assigned to the assignee hereof.

Essentially, in the aforesaid patent application, promoting one of the pathways over the other is described, by the administration of a combination of compounds combining an inhibitor of one of the pathways with a stimulator of the other pathway.

Even more specifically, it has now been shown that the growth of body and/or head hair can be promoted and/or their loss can be controlled by promoting the cyclooxygenase pathway, for example by activating PGHS and inhibiting the lipoxygenase pathway.

The involvement of these enzymes in several metabolic pathways and the consequences which may ensue from deregulating their functioning are such that extensive research has been undertaken in order to develop active agents with the capacity either of increasing or of reducing the activity of these enzymes.

Arachidonic acid metabolites, nitrogen monoxide and nitrogen-monoxide-donating compounds, stanozolol, glutathione-donating compounds, calcium ionophores, anthocyanosides, bioflavonoids, platelet activating factors (PAF), pro-inflammatory cytokines agents and bacterial endotoxins are recognized, in particular, in the field of cyclooxygenase activators.

Similarly, illustrative is 6-chloro-2,3-dihydroxy-1,4-naphthoquinone (CNDQ), which has the particular feature of being both a lipoxygenase inhibitor and a cyclooxygenase stimulator (C. J. Bedord et al., *The Journal of Investigative Dermatology*, 81:566–571 (1983)).

However, most of these species present the major drawback of having a broad functional spectrum, which entails that, in general, they have no genuine specificity for cyclooxygenase. In this regard, the literature on this subject reflects a wide variety of interpretation. These substrates can also be labile or their activity can depend on their concentration, which makes them difficult to administer.

The present inventors have thus sought to develop novel compounds which have activity at least on PGHS, and which would then be considered cyclooxygenase activators.

After considerable research, it has now surprisingly and unexpectedly been determined that the 2-amino-4-alkylaminopyrimidine 3-oxides of the invention have the property of activating PGHS.

Furthermore, the presence of an alkyl chain in the 4-position imparts to these compounds improved lipophilic properties.

This reinforces the advantage of these compounds as active agents in the treatment of hair loss.

Accordingly, this invention features novel compounds corresponding to the structural formula (I):

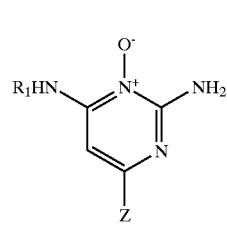

(I)

in which $R_1$ is an alkyl group having from 5 to 20 carbon atoms, and Z is either a hydrogen atom or a radical $-OR_2$, wherein $R_2$ is an alkyl group having from 1 to 12 carbon atoms, as well as the acyl derivatives and acid addition salts thereof.

Consistent herewith, by the term "alkyl radical" is intended a linear or branched acyclic radical originating from the removal of a hydrogen atom in a hydrocarbon molecule, such as, for example, a methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or eicosadecyl radical.

In one preferred embodiment of the invention, $R_1$ is an alkyl radical having from 6 to 12 carbon atoms, such as, for example, a hexyl, heptyl, octyl, nonyl, decyl, undecyl or dodecyl radicals.

In another preferred embodiment of the invention, $R_2$ is an alkyl radical having from 2 to 6 carbon atoms, such as, for example, an ethyl, propyl, butyl, pentyl or hexyl radical.

Preferred compounds of the invention include:

2-amino-4-pentylaminopyrimidine 3-oxide;
2-amino-4-hexylaminopyrimidine 3-oxide;
2-amino-4-heptylaminopyrimidine 3-oxide;
2-amino-4-octylaminopyrimidine 3-oxide;
2-amino-4-nonylaminopyrimidine 3-oxide;
2-amino-4-decylaminopyrimidine 3-oxide;
2-amino-4-undecylaminopyrimidine 3-oxide;
2-amino-4-dodecylaminopyrimidine 3-oxide;
2-amino-4-tridecylaminopyrimidine 3-oxide;
2-amino-4-tetradecylaminopyrimidine 3-oxide;
2-amino-4-pentadecylaminopyrimidine 3-oxide;
2-amino-4-hexadecylaminopyrimidine 3-oxide;
2-amino-4-heptadecylaminopyrimidine 3-oxide;
2-amino-4-octadecylaminopyrimidine 3-oxide;
2-amino-4-nonadecylaminopyrimidine 3-oxide;
2-amino-4-eicosadecylaminopyrimidine 3-oxide;
2-amino-4-pentylamino-6-methoxypyrimidine 3-oxide;
2-amino-4-hexylamino-6-methoxypyrimidine 3-oxide;
2-amino-4-heptylamino-6-methoxypyrimidine 3-oxide;
2-amino-4-octylamino-6-methoxypyrimidine 3-oxide;
2-amino-4-nonylamino-6-methoxypyrimidine 3-oxide;
2-amino-4-decylamino-6-methoxypyrimidine 3-oxide;
2-amino-4-undecylamino-6-methoxypyrimidine 3-oxide;
2-amino-4-dodecylamino-6-methoxypyrimidine 3-oxide;
2-amino-4-tridecylamino-6-methoxypyrimidine 3-oxide;
2-amino-4-tetradecylamino-6-methoxypyrimidine 3-oxide;
2-amino-4-pentadecylamino-6-methoxypyrimidine 3-oxide;
2-amino-4-hexadecylamino-6-methoxypyrimidine 3-oxide;

2-amino-4-heptadecylamino-6-methoxypyrimidine 3-oxide;
2-amino-4-octadecylamino-6-methoxypyrimidine 3-oxide;
2-amino-4-nonadecylamino-6-methoxypyrimidine 3-oxide;
2-amino-4-eicosadecylamino-6-methoxypyrimidine 3-oxide;
2-amino-4-pentylamino-6-ethoxypyrimidine 3-oxide;
2-amino-4-hexylamino-6-ethoxypyrimidine 3-oxide;
2-amino-4-heptylamino-6-ethoxypyrimidine 3-oxide;
2-amino-4-octylamino-6-ethoxypyrimidine 3-oxide;
2-amino-4-nonylamino-6-ethoxypyrimidine 3-oxide;
2-amino-4-decylamino-6-ethoxypyrimidine 3-oxide;
2-amino-4-undecylamino-6-ethoxypyrimidine 3-oxide;
2-amino-4-dodecylamino-6-ethoxypyrimidine 3-oxide;
2-amino-4-tridecylamino-6-ethoxypyrimidine 3-oxide;
2-amino-4-tetradecylamino-6-ethoxypyrimidine 3-oxide;
2-amino-4-pentadecylamino-6-ethoxypyrimidine 3-oxide;
2-amino-4-hexadecylamino-6-ethoxypyrimidine 3-oxide;
2-amino-4-heptadecylamino-6-ethoxypyrimidine 3-oxide;
2-amino-4-octadecylamino-6-ethoxypyrimidine 3-oxide;
2-amino-4-nonadecylamino-6-ethoxypyrimidine 3-oxide;
2-amino-4-eicosadecylamino-6-ethoxypyrimidine 3-oxide;
2-amino-4-pentylamino-6-propyloxypyrimidine 3-oxide;
2-amino-4-hexylamino-6-propyloxypyrimidine 3-oxide;
2-amino-4-heptylamino-6-propyloxypyrimidine 3-oxide;
2-amino-4-octylamino-6-propyloxypyrimidine 3-oxide;
2-amino-4-nonylamino-6-propyloxypyrimidine 3-oxide;
2-amino-4-decylamino-6-propyloxypyrimidine 3-oxide;
2-amino-4-undecylamino-6-propyloxypyrimidine 3-oxide;
2-amino-4-dodecylamino-6-propyloxypyrimidine 3-oxide;
2-amino-4-tridecylamino-6-propyloxypyrimidine 3-oxide;
2-amino-4-tetradecylamino-6-propyloxypyrimidine 3-oxide;
2-amino-4-pentadecylamino-6-propyloxypyrimidine 3-oxide;
2-amino-4-hexadecylamino-6-propyloxypyrimidine 3-oxide;
2-amino-4-heptadecylamino-6-propyloxypyrimidine 3-oxide;
2-amino-4-octadecylamino-6-propyloxypyrimidine 3-oxide;
2-amino-4-nonadecylamino-6-propyloxypyrimidine 3-oxide;
2-amino-4-eicosadecylamino-6-propyloxypyrimidine 3-oxide;
2-amino-4-pentylamino-6-butyloxypyrimidine 3-oxide;
2-amino-4-hexylamino-6-butyloxypyrimidine 3-oxide;
2-amino-4-heptylamino-6-butyloxypyrimidine 3-oxide;
2-amino-4-octylamino-6-butyloxypyrimidine 3-oxide;
2-amino-4-nonylamino-6-butyloxypyrimidine 3-oxide;
2-amino-4-decylamino-6-butyloxypyrimidine 3-oxide;
2-amino-4-undecylamino-6-butyloxypyrimidine 3-oxide;
2-amino-4-dodecylamino-6-butyloxypyrimidine 3-oxide;
2-amino-4-tridecylamino-6-butyloxypyrimidine 3-oxide;
2-amino-4-tetradecylamino-6-butyloxypyrimidine 3-oxide;
2-amino-4-pentadecylamino-6-butyloxypyrimidine 3-oxide;
2-amino-4-hexadecylamino-6-butyloxypyrimidine 3-oxide;
2-amino-4-heptadecylamino-6-butyloxypyrimidine 3-oxide;
2-amino-4-octadecylamino-6-butyloxypyrimidine 3-oxide;
2-amino-4-nonadecylamino-6-butyloxypyrimidine 3-oxide;
2-amino-4-eicosadecylamino-6-butyloxypyrimidine 3-oxide; and Even more preferred compounds according to the invention are:
2-amino-4-hexylaminopyrimidine 3-oxide;
2-amino-4-octylaminopyrimidine 3-oxide;
2-amino-4-dodecylaminopyrimidine 3-oxide;
2-amino-4-octylamino-6-butyloxypyrimidine 3-oxide; and yet even more preferred are
2-amino-4-dodecylaminopyrimidine 3-oxide; and
2-amino-4-octylamino-6-butyloxypyrimidine 3-oxide.

This invention also features a process for preparing the 2-amino-4-alkylaminopyrimidine 3-oxides of formula (I).

This process comprises reacting an aliphatic amine with 2-amino-4,6-dichloropyrimidine in a solvent such as ethanol. The compound thus obtained, after purification, is then reacted with a urea/$H_2O_2$ complex and phthalic anhydride in a solvent such as isopropanol. After purification, the compound obtained is reacted in the presence of potassium hydroxide and palladium-on-charcoal in a solvent such as absolute ethanol, under a hydrogen pressure in order to provide the corresponding 2-amino-4-alkylaminopyrimidine 3-oxides.

The present invention also features a process for preparing the 2-amino-4-alkylamino-6-alkyloxy-pyrimidine 3-oxides of formula (I).

This process comprises reacting an aliphatic amine with 2-amino-4,6-dichloropyrimidine in a solvent such as ethanol. The compound thus obtained, after purification, is then reacted with a urea/$H_2O_2$ complex and phthalic anhydride in a solvent such as isopropanol. After purification, the compound obtained is reacted with an excess of sodium or potassium alkoxide to provide the corresponding 2-amino-4-alkylamino-6-alkyl-oxypyrimidine 3-oxide.

Too, this invention features compositions which comprise at least one compound of the 2-amino-4-alkyl-aminopyrimidine 3-oxides having the structural formula It will of course be appreciated that the compositions according to the invention can contain the compounds of formula (I) either alone or as mixtures in all proportions.

Too, the "effective" amount of compound administered corresponds to the amount required to elicit the desired result. One skilled in this art is thus capable of easily evaluating this effective amount, which depends on the nature of the compound used and on the particular individual thus treated.

To provide an order of magnitude, in the compositions according to the invention, the compounds of formula (I) are advantageously present at a concentration ranging from 0.001% to 10% by weight relative to the total weight of the composition and preferably from 0.01% to 2%.

The present invention also features formulating as an active principle, in a physiologically acceptable medium (vehicle, diluent or carrier), into a composition, of an effective amount of at least one compound of formula (I); such compounds/compositions are well suited to induce and/or stimulate hair growth and/or prevent hair loss.

The compositions according to the invention can be ingested, injected or topically applied onto the skin and/or the hair. Depending on the mode of administration, the compositions according to the invention are formulated into any pharmaceutical form normally employed.

For topical application onto the skin or the hair, the composition can be in the form, in particular, of an aqueous or oily solution or a dispersion of the lotion or serum type, emulsions of liquid or semi-liquid consistency of the milk type, obtained by dispersing a fatty phase in an aqueous phase (O/W) or, conversely, (W/O), or suspensions or emulsions of runny consistency of the cream or aqueous or anhydrous gel type, or alternatively microcapsules or microparticles, or vesicle dispersions of ionic and/or non-ionic type. These compositions are formulated via the usual techniques.

They can also be used for the hair in the form of aqueous, alcoholic or aqueous-alcoholic solutions, or in the form of creams, gels, ointments, emulsions or mousses or alternatively in the form of aerosol compositions also comprising a propellant under pressure.

The compositions according to the invention can also constitute a haircare composition, in particular a shampoo, a hairsetting lotion, a treating lotion, a styling cream or gel, a dye composition (in particular an oxidation dye composition) optionally in the form of coloring shampoos, restructuring lotions for the hair, a permanent-waving composition (in particular a composition for the first stage of a permanent-waving operation), a lotion or gel for preventing hair loss, an antiparasitic shampoo, etc.

For systemic injection, the subject compositions can be formulated as an aqueous or oily lotion or in the form of a serum. For the eyes, drops are well suited, and for ingestion, same can be formulated as capsules, granules, syrups or tablets.

The amounts of the various constituents in the compositions according to the invention are those conventional in the fields under consideration.

The compositions according to the invention can also be formulated as solid preparations constituting cleansing soaps or bars.

The subject compositions can also be packaged in the form of an aerosol composition also comprising a propellant under pressure.

When the composition is an emulsion, the proportion of the fatty phase advantageously ranges from 5% to 80% by weight and preferably from 5% to 50% by weight relative to the total weight of the composition. The oils, waxes, emulsifiers and co-emulsifiers included in the composition in emulsion form are chosen from among those that are conventional in the cosmetics field. The emulsifier and the co-emulsifier are advantageously present in the composition in a proportion ranging from 0.3% to 30% by weight, and preferably from 0.5% to 20% by weight, relative to the total weight of the composition. The emulsion can also contain lipid vesicles.

When the composition is an oily solution or gel, the fatty phase can constitute more than 90% of the total weight of the composition.

In known fashion, the subject compositions can also contain additives and adjuvants that are common in the cosmetics field, such as hydrophilic or lipophilic gelling agents, hydrophilic or lipophilic additives and active agents, preservatives, antioxidants, solvents, fragrances, fillers, sunscreening agents, odor absorbers and dyestuffs and colorants. The amounts of these various adjuvants are those conventionally formulated in the cosmetics field, and, for example, range from 0.01% to 10% of the total weight of the composition. Depending on their nature, these additives and adjuvants can be introduced into the fatty phase, into the aqueous phase and/or into the lipid spherules.

Exemplary oils or waxes according to the invention include mineral oils (liquid petroleum jelly), plant oils (liquid fraction of karite butter or sunflower oil), animal oils (perhydrosqualene), synthetic oils (purcellin oil), silicone oils or waxes (cyclomethicone) and fluoro oils (perfluoropolyethers), beeswax, carnauba wax or paraffin wax. Fatty alcohols and fatty acids (stearic acid) can be added to these oils. Exemplary emulsifiers according to the invention include glyceryl stearate, polysorbate-60 and the PEG-6/PEG-32/glycol stearate mixture marketed under the trademark Tefose®63 by Gattefosse.

Exemplary solvents per this invention include the lower alcohols, in particular ethanol and isopropanol, and propylene glycol.

And exemplary hydrophilic gelling agents include carboxyvinyl polymers (carbomer), acrylic copolymers such as acrylate/alkylacrylate copolymers, polyacrylamides, polysaccharides such as hydroxy-propylcellulose, natural gums and clays, and exemplary lipophilic gelling agents include modified clays such as bentones, metal salts of fatty acids, such as aluminum stearates, and hydrophobic silica, ethylcellulose and polyethylene.

The subject compositions can contain other hydrophilic active agents, such as proteins or protein hydrolysates, amino acids, polyols, urea, allantoin, sugars and sugar derivatives, water-soluble vitamins, plant extracts and hydroxy acids.

Lipophilic active agents which are suitable include retinol (vitamin A) and derivatives thereof, tocopherol (vitamin E) and derivatives thereof, essential fatty acids, ceramides, essential oils and salicylic acid and its derivatives.

In one embodiment according to the invention, the subject compositions comprise at least one compound of formula (I) in admixture with other active agents. Among these active agents, particularly representative are:

(1) agents for improving the activity with regard to regrowth of the hair and/or preventing hair loss, and which have already been described for such activity, for example, nicotinic acid esters, including, in particular, tocopheryl nicotinate, benzyl nicotinate and $C_1$–$C_6$ alkyl nicotinates such as methyl or hexyl nicotinates, pyrimidine derivatives, such as 2,4-diamino-6-piperidinopyrimidine 3-oxide or "Minoxidil" described in U.S. Pat. Nos. 4,139,619 and 4,596,812, and agents for promoting regrowth of the hair, such as those described in the European patent application published under No. 0,648,488 and assigned to the assignee hereof;

(2) agents which reduce skin differentiation and/or proliferation and/or pigmentation, such as retinoic acid and its isomers, retinol and its esters, vitamin D and derivatives thereof, estrogens such as estradiol, kojic acid or hydroquinone;

(3) antibacterial agents such as clindamycin phosphate, erythromycin or antibiotics of the tetracyclene class;

(4) antiparasitic agents, in particular metronidazole, crotamiton or pyrethroids;

(5) antifungal agents, in particular compounds belonging to the imidazole class, such as econazole, ketoconazole or miconazole or their salts, polyene compounds, such as amphotericin B, compounds of the allylamine family such as terbinafine, or alternatively octopirox;

(6) antiviral agents such as acyclovir;

(7) steroidal anti-inflammatory agents such as hydrocortisone, betamethasone valerate or clobetasol propionate, or nonsteroidal anti-inflammatory agents such as, for example, ibuprofen and its salts, diclofenac and its salts, acetylsalicylic acid, acetaminophen or glycyrrhizic acid;

(8) anaesthetics such as lidocane hydrochloride and derivatives thereof;

(9) anti-pruriginous agents such as thenaldine, trimeprazine or cyproheptadine;

(10) keratolytic agents such as α- and β-hydroxycarboxylic or β-ketocarboxylic acids, their salts, amides or esters and more particularly hydroxy acids such as glycolic acid, lactic acid, salicylic acid, citric acid and fruit acids in general, and 5-n-octanoylsalicylic acid;

(11) anti-free-radical agents such as α-tocopherol or its esters, superoxide dismutases, certain metal-chelating agents or ascorbic acid and its esters;

(12) antiseborrhoeic agents such as progesterone;

(13) antidandruff agents such as octopirox or zinc pyrithione;

(14) antiacne agents such as retinoic acid or benzoyl peroxide;

(15) extracts of plant, marine or bacterial origin.

Other compounds may also be included, for example, Diazoxide, Spiroxazone, phospholipids such as lecithin, linoleic acid, linolenic acid, salicylic acid and derivatives thereof described in FR-2,581,542, e.g., salicylic acid derivatives bearing an alkanoyl group containing from 2 to 12 carbon atoms in the 5-position of the benzene ring, hydroxycarboxylic or ketocarboxylic acids and their esters, lactones and their corresponding salts, anthralin, carotenoids, eicosatetraenoic and eicosatrienoic acids or their esters and amides.

Thus, in one specific embodiment, the compositions according to the invention also comprise at least one active agent or substrate selected from among antibacterial agents, antiparasitic agents, antifungal agents, antiviral agents, anti-inflammatory agents, antipruriginous agents, anaesthetics, keratolytic agents, anti-free-radical agents, antiseborrhoeic agents, antidandruff agents, antiacne agents and/or agents for reducing skin differentiation and/or proliferation and/or pigmentation, and extracts of plant, marine or bacterial origin.

It will also be appreciated that the subject compositions can comprise at least one compound as described above in liposomal form, in particular as described in WO-94/22468, filed Oct. 13, 1994 by Anti Cancer Inc. Thus, the compound encapsulated in the liposomes can be delivered selectively to the hair follicle.

The compositions according to the invention are topically applied onto the alopecic areas of an individual subject's scalp and hair, and is optionally maintained in contact with such areas for several hours and optionally rinsed therefrom. In one embodiment, a composition containing an effective amount of at least one compound as described above is topically applied during the evening, maintained overnight and optionally shampooed out in the morning. These applications can be repeated daily for one or more months depending on the needs of the individual.

Thus, the present invention also features a cosmetic treatment for the hair and/or the scalp (regime or regimen), comprising topically applying a composition containing an effective amount of at least one compound as described above to the hair and/or the scalp, maintaining this composition in contact with the hair and/or the scalp and optionally rinsing same therefrom.

This treatment has the characteristics of a cosmetic regime/regimen inasmuch as it improves the aesthetics of the hair by providing more vitality and imparting an improved appearance thereto.

The compositions according to the invention are well suited for cosmetic or pharmaceutical applications, in particular dermatological application.

In order to further illustrate the present invention and the advantages thereof, the following specific examples are given, it being understood that same are intended only as illustrative and in nowise limitative.

EXAMPLE 1

Synthesis of 2-Amino-4-hexylaminopyrimidine 3-Oxide

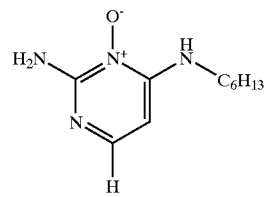

(1) Preparation of 2-Amino-4-hexylamino-6-chloro-pyrimidine:

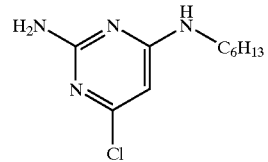

50 g of 2-amino-4,6-dichloropyrimidine were suspended in 350 ml of absolute ethanol in a reactor. 181.5 ml of hexylamine (reagent A) were added in a single portion and the mixture was refluxed for 3 h. The medium was evaporated under vacuum. The oil obtained was taken up in 600 ml of water with stirring for 1 h, 30 min. The precipitate was filtered off, washed and dried in a heated desiccator. 43.5 g of the expected compound were thus obtained, for a yield of 62%.

Analysis:

NMR spectrum: $^1$H (200 MHz; DMSO) δ ppm 0.8 (3H, t), 1.2 (6H, s), 1.4 (2H, t), 3(2H, s), 5.6 (1H, s), 6.2 (2H, s), 6.9 (1H, s).

(2) Preparation of 2-Amino-4-hexylamino-6-chloro-pyrimidine 3-Oxide:

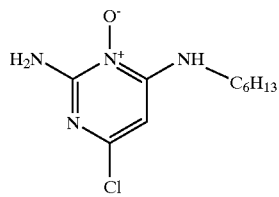

5.95 g of urea/H₂O₂ complex and 9.07 g of phthalic anhydride were suspended in 90 ml of isopropanol, in a three-necked flask. The mixture was stirred for 30 min at room temperature (20–25° C.). 10 g of 2-amino-4-hexylamino-6-chloropyrimidine were then added while controlling the exotherm at +30° C. After reaction for 3 hours, 100 ml of sodium hydrogen sulfite were poured thereinin to destroy the residual oxidizing agents. The mixture was permitted to separate out by settling and the upper phase was concentrated under vacuum. The residue obtained was taken up in a water (80 ml)/30% sodium hydroxide (20 ml) mixture. The solid obtained was reimpasted in 150 ml of isopropyl ether. The solid was filtered off and washed. It was dried in a heated desiccator. 4.52 g of the expected compound were thus obtained, for a yield of 42%.

Analysis:

NMR spectrum ¹H (200 MHz; DMSO) δ ppm 0.7 (3H, t), 1 (6H, s), 1.2 (2H, t), 3.1(2H, m), 6 (1H, s), 7.4 (2H, m), 7.7 (1H, t).

(3) Synthesis of 2-Amino-4-hexylaminopyrimidine 3-Oxide:

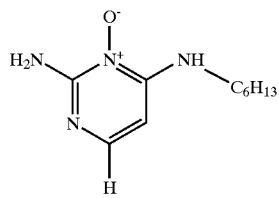

0.7 g of potassium hydroxide was dissolved in 100 ml of absolute ethanol, in a three-necked flask. 2.2 g of 2-amino-4-hexylamino-6-chloropyrimidine 3-oxide were then added. After complete dissolution, 0.5 g of palladium-on-charcoal was added and the mixture was reacted in a hydrogenator at a hydrogen pressure of 3 bar. After 2 hours, the medium was filtered through filter paper and concentrated under vacuum. The pale yellow solid obtained was recrystallized from 20 ml of acetonitrile. It was filtered off and the filter cake was washed with 10 ml of water. The solid was dried in a desiccator under vacuum. 1 g of the expected compound was thus obtained, for a yield of 53%.

Analysis:

NMR spectrum: ¹H (200 MHz; DMSO) δ ppm; 1.9 (3H, t), 2.2 (6H, s), 2.5 (2H, t), 4.3 (2H, m), 7.2 (1H, d), 8.1 (2H, s), 8.5 (1H, d), 8.6 (1H, m).

EXAMPLE 2

Synthesis of 2-Amino-4-dodecylaminopyrimidine 3-Oxide

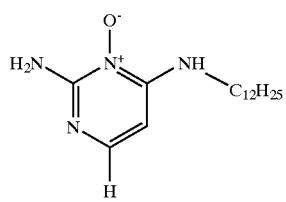

(1) Preparation of 2-Amino-4-dodecylamino-6-chloro-pyrimidine:

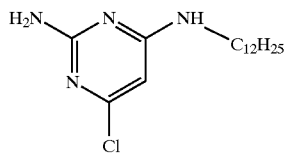

10 g of 2-amino-4,6-dichloropyrimidine were suspended in 100 ml of absolute ethanol in a reactor. 33.9 g of dodecylamine (reagent A) were added in a single portion and the mixture was refluxed for 2 h. The medium was evaporated under vacuum. The solid obtained was taken up in 200 ml of acetone with stirring for 30 min. 200 ml of water were added and the mixture was maintained under stirring for 2 h. The solid was filtered off, washed and dried in a heated desiccator.

17.55 g of the expected compound were thus obtained, for a yield of 92%.

Analysis:

NMR spectrum: ¹H (200 MHz; DMSO) δ ppm; 0.8 (3H, t), 1.2 (18H, s), 1.3 (2H, t), 3 (2H, s), 5.6 (1H, s), 6.1 (2H, s), 6.8 (1H, s).

(2) Preparation of 2-Amino-4-dodecylamino-6-chloro-pyrimidine 3-Oxide:

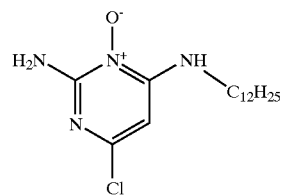

3.26 9 of urea/H₂O₂ complex and 4.97 g of phthalic anhydride were suspended in 60 ml of isopropanol, in a three-necked flask. The mixture was maintained under stirring for 30 min at room temperature. 10 g of 2-amino-4-dodecylamino-6-chloropyrimidine were then added while controlling the exotherm at +25° C. After reaction for 2 hours, the medium was cooled to +40° C. for 1 h. The solid was filtered off and washed with 5 ml of ice-cold methanol. The solid was taken up in a water (12 ml)/40% sodium hydroxide (3 ml) mixture. The solid was filtered off and washed. It was dried in a heated desiccator.

3.3 g of the expected compound were thus obtained, for a yield of 42%.

Analysis:

NMR spectrum ¹H (200 MHz; DMSO) δ ppm; 0.7 (3H, t), 1.1 (18H, s), 1.3 (2H, t), 2.8 (2H, t), 5.5 (1H, s), 6.9 (3H, m).

(3) Synthesis of 2-Amino-4-dodecylaminopyrimidine 3-Oxide:

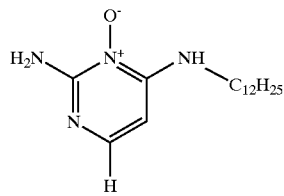

0.7 g of potassium hydroxide was dissolved in 250 ml of absolute ethanol, in a three-necked flask. 3.3 g of 2-amino-4-dodecylamino-6-chloropyrimidine 3-oxide were then added. Once dissolution was complete, 0.5 g of palladium-on-charcoal was added and the mixture was reacted in a hydrogenator at a hydrogen pressure of 3 bar. After 2 h, the medium was filtered through filter paper and concentrated under vacuum. The solid obtained was recrystallized from an ethanol (10 ml)/acetonitrile (50 ml) mixture. It was filtered off and the filter cake was washed with 10 ml of water. The solid was dried in a desiccator under vacuum.

0.8 g of the expected compound was thus obtained, for a yield of 27%.

Analysis:

NMR spectrum: $^1$H (200 MHz; DMSO) δ ppm; 0.9 (3H, t), 1.3 (18H, s), 1.7 (2H, t), 3.3 (2H, m), 6.3 (1H, d), 7.2 (2H, s), 7.6 (1H, d), 7.7 (1H, m).

EXAMPLE 3

Synthesis of 2-Amino-4-octylaminopyrimidine 3-Oxide

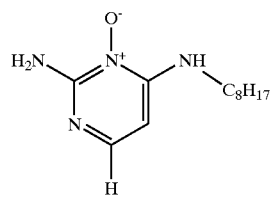

(1) Preparation of 2-Amino-4-octylamino-6-chloropyrimidine:

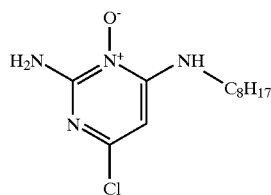

20 g of 2-amino-4,6-dichloropyrimidine were suspended in 200 ml of absolute ethanol in a reactor. 60 g of octylamine (reagent A) were added in a single portion and the mixture was refluxed for 2 h. The medium was evaporated under vacuum. The oil obtained was extracted with dichloromethane and was then purified on a column of silica.

22.8 g of the expected compound were thus obtained, for a yield of 71%.

Analysis:

NMR: $^1$H (200 MHz; CDCl$_3$) δ ppm; 1 (3H, t), 1.4 (10H, s), 1.7 (2H, t), 3.3 (2H, m), 5.1 (3H, d), 6 (1H, s)

(2) Preparation of 2-Amino-4-octylamino-6-chloropyrimidine 3-Oxide:

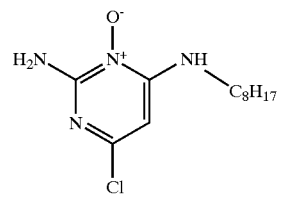

6.8 g of urea/H$_2$O$_2$ complex and 10.35 g of phthalic anhydride were suspended in 100 ml of isopropanol, in a three-necked flask. The mixture was maintained stirring for 30 min at room temperature. 10 g of 2-amino-4-octylamino-6-chloropyrimidine were then added, while controlling the exotherm at +30° C. After reaction for 3 hours, 100 ml of sodium hydrogen sulfite were poured thereinin to destroy the residual oxidizing agents. The mixture was permitted to separate by settling and the upper phase was concentrated under vacuum. The residue obtained was taken up in a water (80 ml)/30% sodium hydroxide (20 ml) mixture. The solid was filtered off and washed. This solid was dried in a heated desiccator.

6.3 g of the expected compound were thus obtained, for a yield of 46%.

Analysis:

NMR: $^1$H (200 MHz; DMSO) δ ppm; 0.7 (3H, t), 1.1 (10H, s), 1.4 (2H, t), 3(2H, t), 6 (1H, s), 7.2 (3H, s).

(3) Synthesis of 2-Amino-4-octylaminopyrimidine

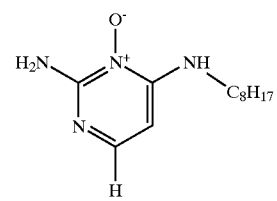

0.54 g of potassium hydroxide was dissolved in 100 ml of absolute ethanol, in a three-necked flask. 2 g of 2-amino-4-octylamino-6-chloropyrimidine 3-oxide were then added. Once dissolution was complete, 0.5 g of palladium-on-charcoal was added and the mixture was reacted in a hydrogenator at a hydrogen pressure of 3 bar. After 2 hours, the medium was filtered through filter paper and concentrated under vacuum. The pale yellow solid obtained was recrystallized from 20 ml of acetonitrile. It was filtered off and the filter cake was washed with 10 ml of water. The solid was dried in a desiccator under vacuum.

0.5 g of the expected compound was thus obtained, for a yield of 29%.

Analysis:

NMR: $^1$H (200 MHz; DMSO) δ ppm; 1.1 (3H, t), 1.4 (10H, s), 1.8 (2H, t), 3.4 (2H, m), 6.1 (1H, d), 6.4 (2H, s), 7.3 (1H, t), 7.7 (1H, d).

EXAMPLES 4–16

The following compounds of the invention listed below are obtained via the same procedure as in Examples 1–3 and using the appropriate reagent A in the first step of the process (see Table I below):

TABLE I

| Compound obtained | Reagent A used |
| --- | --- |
| 4 2-amino-4-pentylaminopyrimidine 3-oxide | pentylamine |
| 5 2-amino-4-heptylaminopyrimidine 3-oxide | heptylamine |
| 6 2-amino-4-nonylaminopyrimidine 3-oxide | nonylamine |
| 7 2-amino-4-decylaminopyrimidine 3-oxide | decylamine |
| 8 2-amino-4-undecylaminopyrimidine 3-oxide | undecylamine |
| 9 2-amino-4-tridecylaminopyrimidine 3-oxide | tridecylamine |
| 10 2-amino-4-tetradecylaminopyrimidine 3-oxide | tetradecylamine |
| 11 2-amino-4-pentadecylaminopyrimidine 3-oxide | pentadecylamine |
| 12 2-amino-4-hexadecylaminopyrimidine 3-oxide | hexadecylamine |
| 13 2-amino-4-heptadecylaminopyrimidine 3-oxide | heptadecylamine |
| 14 2-amino-4-octadecylaminopyrimidine 3-oxide | octadecylamine |
| 15 2-amino-4-nonadecylaminopyrimidine 3-oxide | nonadecylamine |
| 16 2-amino-4-eicosadecylaminopyrimidine 3-oxide | eicosadecyl-amine |

EXAMPLE 17

Synthesis of 2-Amino-4-octylamino-6-butyloxypyrimidine 3-Oxide

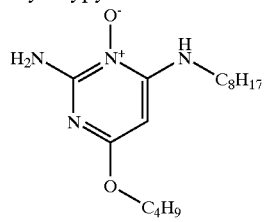

90 ml of butanol (reagent B) predried over $K_2CO_3$ were introduced into a 250 ml three-necked flask. 0.18 g of sodium in kerosene was added portionwise under argon. The medium was then heated at 60° C. until the sodium has completely dissolved.

1.5 g of 2-amino-4-octylamino-6-chloro-pyrimidine 3-oxide, obtained according to Example 3 (reagent C), was then introduced and the mixture was heated at 90° C. for 24 hours.

The medium was washed with aqueous 20% sodium chloride solution and the butanol phase was then concentrated on a rotavapor. The residue obtained was purified on a column of silica. The oily product obtained at the column outlet was dissolved in 2.2 ml (2.5 eq) of 2N hydrochloric methanol solution and the solution was then evaporated under reduced pressure. An off-white solid was obtained, which was washed with 10 ml of isopropyl ether. 0.5 g of a white solid of the expected compound was obtained, in a yield of 30%.

Analysis:

NMR: $^1H$ (200 MHz; DMSO) δ ppm; 1 (6H, m), 1.7 (2H, s), 6.1 (16H, m), 3.4 (2H, q), 4.3 (2H; t), 5.7 (1H; s), 8.5 (4H; m).

Elemental analysis (1 Hcl):

|  | C | H | N | O | Cl |
| --- | --- | --- | --- | --- | --- |
| Theoretical | 55.40% | 9.01% | 16.15% | 9.22% | 10.22% |
| Found | 55.19% | 8.88% | 16.07% | 9.94% |  |

EXAMPLES 18 to 80

The following compounds of the invention listed below (Table II) are obtained via the same procedure as in Example 17, but using the appropriate reagent A in the first step of the process and the appropriate reagents B and C in the 2nd step (see Table III below).

TABLE II

| Example | Compound obtained |
| --- | --- |
| 18 | 2-amino-4-pentylamino-6-methoxypyrimidine 3-oxide |
| 19 | 2-amino-4-hexylamino-6-methoxypyrimidine 3-oxide |
| 20 | 2-amino-4-heptylamino-6-methoxypyrimidine 3-oxide |
| 21 | 2-amino-4-octylamino-6-methoxypyrimidine 3-oxide |
| 22 | 2-amino-4-nonylamino-6-methoxypyrimidine 3-oxide |
| 23 | 2-amino-4-decylamino-6-methoxypyrimidine 3-oxide |
| 24 | 2-amino-4-undecylamino-6-methoxypyrimidine 3-oxide |
| 25 | 2-amino-4-dodecylamino-6-methoxypyrimidine 3-oxide |
| 26 | 2-amino-4-tridecylamino-6-methoxypyrimidine 3-oxide |
| 27 | 2-amino-4-tetradecylamino-6-methoxypyrimidine 3-oxide |
| 28 | 2-amino-4-pentadecylamino-6-methoxypyrimidine 3-oxide |
| 29 | 2-amino-4-hexadecylamino-6-methoxypyrimidine 3-oxide |
| 30 | 2-amino-4-heptadecylamino-6-methoxypyrimidine 3-oxide |
| 31 | 2-amino-4-octadecylamino-6-methoxypyrimidine 3-oxide |
| 32 | 2-amino-4-nonadecylamino-6-methoxypyrimidine 3-oxide |
| 33 | 2-amino-4-eicosadecylamino-6-methoxypyrimidine 3-oxide |
| 34 | 2-amino-4-pentylamino-6-ethoxypyrimidine 3-oxide |
| 35 | 2-amino-4-hexylamino-6-ethoxypyrimidine 3-oxide |
| 36 | 2-amino-4-heptylamino-6-ethoxypyrimidine 3-oxide |
| 37 | 2-amino-4-octylamino-6-ethoxypyrimidine 3-oxide |
| 38 | 2-amino-4-nonylamino-6-ethoxypyrimidine 3-oxide |
| 39 | 2-amino-4-decylamino-6-ethoxypyrimidine 3-oxide |
| 40 | 2-amino-4-undecylamino-6-ethoxypyrimidine 3-oxide |
| 41 | 2-amino-4-dodecylamino-6-ethoxypyrimidine 3-oxide |
| 42 | 2-amino-4-tridecylamino-6-ethoxypyrimidine 3-oxide |
| 43 | 2-amino-4-tetradecylamino-6-ethoxypyrimidine 3-oxide |
| 44 | 2-amino-4-pentadecylamino-6-ethoxypyrimidine 3-oxide |
| 45 | 2-amino-4-hexadecylamino-6-ethoxypyrimidine 3-oxide |
| 46 | 2-amino-4-heptadecylamino-6-ethoxypyrimidine 3-oxide |
| 47 | 2-amino-4-octadecylamino-6-ethoxypyrimidine 3-oxide |
| 48 | 2-amino-4-nonadecylamino-6-ethoxypyrimidine 3-oxide |
| 49 | 2-amino-4-eicosadecylamino-6-ethoxypyrimidine 3-oxide |
| 50 | 2-amino-4-pentylamino-6-propyloxypyrimidine 3-oxide |
| 51 | 2-amino-4-hexylamino-6-propyloxypyrimidine 3-oxide |
| 52 | 2-amino-4-heptylamino-6-propyloxypyrimidine 3-oxide |
| 53 | 2-amino-4-octylamino-6-propyloxypyrimidine 3-oxide |
| 54 | 2-amino-4-nonylamino-6-propyloxypyrimidine 3-oxide |
| 55 | 2-amino-4-decylamino-6-propyloxypyrimidine 3-oxide |
| 56 | 2-amino-4-undecylamino-6-propyloxypyrimidine 3-oxide |
| 57 | 2-amino-4-dodecylamino-6-propyloxypyrimidine 3-oxide |
| 58 | 2-amino-4-tridecylamino-6-propyloxypyrimidine 3-oxide |
| 59 | 2-amino-4-tetradecylamino-6-propyloxypyrimidine 3-oxide |
| 60 | 2-amino-4-pentadecylamino-6-propyloxypyrimidine 3-oxide |
| 61 | 2-amino-4-hexadecylamino-6-propyloxypyrimidine 3-oxide |
| 62 | 2-amino-4-heptadecylamino-6-propyloxypyrimidine 3-oxide |
| 63 | 2-amino-4-octadecylamino-6-propyloxypyrimidine 3-oxide |
| 64 | 2-amino-4-nonadecylamino-6-propyloxypyrimidine 3-oxide |
| 65 | 2-amino-4-eicosadecylamino-6-propyloxypyrimidine 3-oxide |
| 66 | 2-amino-4-pentylamino-6-butyloxypyrimidine 3-oxide |
| 67 | 2-amino-4-hexylamino-6-butyloxypyrimidine 3-oxide |
| 68 | 2-amino-4-heptylamino-6-butyloxypyrimidine 3-oxide |
| 69 | 2-amino-4-nonylamino-6-butyloxypyrimidine 3-oxide |
| 70 | 2-amino-4-decylamino-6-butyloxypyrimidine 3-oxide |
| 71 | 2-amino-4-undecylamino-6-butyloxypyrimidine 3-oxide |
| 72 | 2-amino-4-dodecylamino-6-butyloxypyrimidine 3-oxide |
| 73 | 2-amino-4-tridecylamino-6-butyloxypyrimidine 3-oxide |
| 74 | 2-amino-4-tetradecylamino-6-butyloxypyrimidine 3-oxide |
| 75 | 2-amino-4-pentadecylamino-6-butyloxypyrimidine 3-oxide |
| 76 | 2-amino-4-hexadecylamino-6-butyloxypyrimidine 3-oxide |
| 77 | 2-amino-4-heptadecylamino-6-butyloxypyrimidine 3-oxide |
| 78 | 2-amino-4-octadecylamino-6-butyloxypyrimidine 3-oxide |
| 79 | 2-amino-4-nonadecylamino-6-butyloxypyrimidine 3-oxide |
| 80 | 2-amino-4-eicosadecylamino-6-butyloxypyrimidine 3-oxide |

TABLE III

| Example | Reagent A | Reagent B | Reagent C |
|---|---|---|---|
| 18 | pentylamine | methanol | 2-amino-4-pentylamino-6-chloro-pyrimidine 3-oxide |
| 19 | hexylamine | methanol | 2-amino-4-hexylamino-6-chloro-pyrimidine 3-oxide |
| 20 | heptylamine | methanol | 2-amino-4-heptylamino-6-chloro-pyrimidine 3-oxide |
| 21 | octylamine | methanol | 2-amino-4-octylamino-6-chloro-pyrimidine 3-oxide |
| 22 | nonylamine | methanol | 2-amino-4-nonylamino-6-chloro-pyrimidine 3-oxide |
| 23 | decylamine | methanol | 2-amino-4-decylamino-6-chloro-pyrimidine 3-oxide |
| 24 | undecylamine | methanol | 2-amino-4-undecylamino-6-chloro-pyrimidine 3-oxide |
| 25 | dodecylamine | methanol | 2-amino-4-dodecylamino-6-chloropyrimidine 3-oxide |
| 26 | tridecylamine | methanol | 2-amino-4-tridecylamino-6-chloro-pyrimidine 3-oxide |
| 27 | tetradecylamine | methanol | 2-amino-4-tetradecylamino-6-chloro-pyrimidine 3-oxide |
| 28 | pentadecylamine | methanol | 2-amino-4-pentadecylamino-6-chloro-pyrimidine 3-oxide |
| 29 | hexadecylamine | methanol | 2-amino-4-hexadecylamino-6-chloro-pyrimidine 3-oxide |
| 30 | heptadecylamine | methanol | 2-amino-4-heptadecylamino-6-chloro-pyrimidine 3-oxide |
| 31 | octadecylamine | methanol | 2-amino-4-octadecylamino-6-chloro-pyrimidine 3-oxide |
| 32 | nonadecylamine | methanol | 2-amino-4-nonadecylamino-6-chloro-pyrimidine 3-oxide |
| 33 | eicosadecylamine | methanol | 2-amino-4-eicosadecylamino-6-chloropyrimidine 3-oxide |
| 34 | pentylamine | ethanol | 2-amino-4-pentylamino-6-chloro-pyrimidine 3-oxide |
| 35 | hexylamine | ethanol | 2-amino-4-hexylamino-6-chloro-pyrimidine 3-oxide |
| 36 | heptylamine | ethanol | 2-amino-4-heptylamino-6-chloro-pyrimidine 3-oxide |
| 37 | octylamine | ethanol | 2-amino-4-octylamino-6-chloro-pyrimidine 3-oxide |
| 38 | nonylamine | ethanol | 2-amino-4-nonylamino-6-chloro-pyrimidine 3-oxide |
| 39 | decylamine | ethanol | 2-amino-4-decylamino-6-chloro-pyrimidine 3-oxide |
| 40 | undecylamine | ethanol | 2-amino-4-undecylamino-6-chloro-pyrimidine 3-oxide |
| 41 | dodecylamine | ethanol | 2-amino-4-dodecylamino-6-chloro-pyrimidine 3-oxide |
| 42 | tridecylamine | ethanol | 2-amino-4-tridecylamino-6-chloro-pyrimidine 3-oxide |
| 43 | tetradecylamine | ethanol | 2-amino-4-tetradecylamino-6-chloro-pyrimidine 3-oxide |
| 44 | pentadecylamine | ethanol | 2-amino-4-pentadecylamino-6-chloro-pyrimidine 3-oxide |
| 45 | hexadecylamine | ethanol | 2-amino-4-hexadecylamino-6-chloro-pyrimidine 3-oxide |
| 46 | heptadecylamine | ethanol | 2-amino-4-heptadecylamino-6-chloro-pyrimidine 3-oxide |
| 47 | octadecylamine | ethanol | 2-amino-4-octadecylamino-6-chloro-pyrimidine 3-oxide |
| 48 | nonadecylamine | ethanol | 2-amino-4-nonadecylamino-6-chloro-pyrimidine 3-oxide |
| 49 | eicosadecylamine | ethanol | 2-amino-4-eicosadecylamino-6-chloropyrimidine 3-oxide |
| 50 | pentylamine | propanol | 2-amino-4-pentylamino-6-chloro-pyrimidine 3-oxide |
| 51 | hexylamine | propanol | 2-amino-4-hexylamino-6-chloro-pyrimidine 3-oxide |
| 52 | heptylamine | propanol | 2-amino-4-heptylamino-6-chloro-pyrimidine 3-oxide |
| 53 | octylamine | propanol | 2-amino-4-octylamino-6-chloro-pyrimidine 3-oxide |
| 54 | nonylamine | propanol | 2-amino-4-nonylamino-6-chloro-pyrimidine 3-oxide |
| 55 | decylamine | propanol | 2-amino-4-decylamino-6-chloro-pyrimidine 3-oxide |
| 56 | undecylamine | propanol | 2-amino-4-undecylamino-6-chloro-pyrimidine 3-oxide |
| 57 | dodecylamine | propanol | 2-amino-4-dodecylamino-6-chloro-pyrimidine 3-oxide |
| 58 | tridecylamine | propanol | 2-amino-4-tridecylamino-6-chloro-pyrimidine 3-oxide |
| 59 | tetradecylamine | propanol | 2-amino-4-tetradecylamino-6-chloro-pyrimidine 3-oxide |
| 60 | pentadecylamine | propanol | 2-amino-4-pentadecylamino-6-chloro-pyrimidine 3-oxide |
| 61 | hexadecylamine | propanol | 2-amino-4-hexadecylamino-6-chloro-pyrimidine 3-oxide |
| 62 | heptadecylamine | propanol | 2-amino-4-heptadecylamino-6-chloro-pyrimidine 3-oxide |
| 63 | octadecylamine | propanol | 2-amino-4-octadecylamino-6-chloro-pyrimidine 3-oxide |
| 64 | nonadecylamine | propanol | 2-amino-4-nonadecylamino-6-chloro-pyrimidine 3-oxide |
| 65 | eicosadecylamine | propanol | 2-amino-4-eicosadecylamino-6-chloropyrimidine 3-oxide |
| 66 | pentylamine | butanol | 2-amino-4-pentylamino-6-chloro-pyrimidine 3-oxide |
| 67 | hexylamine | butanol | 2-amino-4-hexylamino-6-chloro-pyrimidine 3-oxide |
| 68 | heptylamine | butanol | 2-amino-4-heptylamino-6-chloro-pyrimidine 3-oxide |
| 69 | nonylamine | butanol | 2-amino-4-nonylamino-6-chloro-pyrimidine 3-oxide |
| 70 | decylamine | butanol | 2-amino-4-decylamino-6-chloro-pyrimidine 3-oxide |
| 71 | undecylamine | butanol | 2-amino-4-undecylamino-6-chloro-pyrimidine 3-oxide |
| 72 | dodecylamine | butanol | 2-amino-4-dodecylamino-6-chloro-pyrimidine 3-oxide |
| 73 | tridecylamine | butanol | 2-amino-4-tridecylamino-6-chloro-pyrimidine 3-oxide |
| 74 | tetradecylamine | butanol | 2-amino-4-tetradecylamino-6-chloro-pyrimidine 3-oxide |
| 75 | pentadecylamine | butanol | 2-amino-4-pentadecylamino-6-chloro-pyrimidine 3-oxide |
| 76 | hexadecylamine | butanol | 2-amino-4-hexadecylamino-6-chloro-pyrimidine 3-oxide |
| 77 | heptadecylamine | butanol | 2-amino-4-heptadecylamino-6-chloro-pyrimidine 3-oxide |
| 78 | octadecylamine | butanol | 2-amino-4-octadecylamino-6-chloro-pyrimidine 3-oxide |
| 79 | nonadecylamine | butanol | 2-amino-4-nonadecylamino-6-chloro-pyrimidine 3-oxide |
| 80 | eicosadecylamine | butanol | 2-amino-4-eicosadecylamino-6-chloropyrimidine 3-oxide |

EXAMPLE 81

Measurement of the Prostaglandin-endoperoxide Synthase (PGHS-1) Activating Power General measuring principles:

The amount of oxygen required for the oxidation of arachidonic acid was measured by means of the cyclooxygenase activity of the prostaglandin-endo-peroxide synthase, in the presence or absence of the test compound.

The oxygen consumption measurements were taken using a Clark electrode connected to a YSI 5300 oxymeter marketed by Yellow Spring Instruments.

These measurements were taken in an open chamber with constant stirring at a temperature of 37° C.

If a graph recorder was used, the oxygen consumption measurement is expressed in the form of a curve, the maximum slope of which makes it possible to determine the initial rate of the reaction, and from which it is possible to calculate the period for which the initial reaction rate is maintained.

The curve thus obtained, in the absence of any substance other than the ingredients required for the enzymatic reaction, provides the basal activity of the enzyme. The initial rate and the period for which this rate is maintained can be determined under these conditions in a reaction comprising only the enzyme and its substrate.

These data will serve as a reference in the study of the test compounds.

The activity of the test compounds was measured under the same conditions, by adding the test compound to the reaction medium. The activity of the test compound with respect to cyclooxygenase was evaluated by means of the variation of the slope and the variation of the period for which the maximum rate was maintained.

Formulation for the measurements:

A solution of 0.1 M Tris and 5 mM EDTA at pH=8.00 (TE solution) was prepared.

The measurements were taken in a buffered solution (TEA buffer) composed of 9 volumes of TE solution and 1 volume of 20% alcohol.

The substrate was formulated in the form of a stock solution of potassium arachidonate according to the supplier's procedure (Interchim, France).

The solution thus obtained had a 46 mM titre of arachidonic acid. It can be stored at 4° C. for 24 hours.

The enzyme employed was prostaglandin endoperoxidesynthase (PGHS-1), isolated from sheep seminal glands, marketed by Cayman Chemical under the reference 60100.

The test compounds were prepared in the form of a stock solution with a titre of 5 mM, in a water/alcohol mixture (80/20) and were tested with the same batch of enzyme.

Measurements

Basal Activities of the Enzyme:

At t=0, 380 µl of TEA buffer preheated to 37° C. were introduced into the measuring chamber and maintained to equilibrate for at least one minute.

At t=1, 300 units of enzyme (PGHS) were introduced.

Recording was initiated, and the mixture was again permitted to stabilize for one minute. The recording obtained provided the reaction baseline.

After a further minute, 10 µl of substrate were introduced and the oxygen consumption was recorded for 2 to 3 minutes.

The initial reaction rate and the period for which this rate was maintained were thus determined. These data served as a reference for the measurements of the activity of the test compounds.

Activities of the Test Compounds:

The experimental conditions were identical to those above, except that the TEA buffer preheated to 37° C. was replaced by an identical buffer containing the test compound at a concentration of 0.5 mM.

Results:

The following results are expressed as a % relative to the values obtained with the control.

TABLE IV

| Compounds | Activation |
| --- | --- |
| Control | +0% |
| Compound of Example 1 | +37% |
| Compound of Example 2 | +11% |
| Compound of Example 3 | +14% |

TABLE IV-continued

| Compounds | Activation |
| --- | --- |
| Compound of Example 17 | +8% |
| Indomethacin[1] | −100% |

[1]: 1-(4-chlorobenzoyl)-5-methoxy-2-methyl-1H-indole-3-acetic acid, or indomethacin, is a known inhibitor of cyclooxygenase activity. (H. P. Rang/M. M. Dale Pharmacology second edition 1991. Published by Churchill Livingstone). This inhibitory effect was clearly evident under the conditions of the experiment.

EXAMPLE 82

The following specific compositions containing at least one 2-amino-4-alkylaminopyrimidine 3-oxide of the invention were formulated employing conventional techniques in the cosmetics or pharmacy arts.

Lotion for preventing hair loss:

| | |
| --- | --- |
| Compound of Example 2 | 0.5 g |
| Propylene glycol | 10.0 g |
| Isopropyl alcohol | qs 100.0 g |

1 ml of this lotion is applied to the scalp, at a frequency of once or twice a day.

| | |
| --- | --- |
| Chimexane NS ® | 1.8 g |
| Monosodium stearylglutamate | 0.2 g |
| Compound of Example 17 | 2.0 g |
| Carbomer | 0.2 g |
| Triethanolamine | qs pH = 7 |
| Preservatives | qs |
| Fragrances | qs |
| Demineralized water | qs 100.0 g |

This gel is applied to the scalp once or twice a day.

Lotion for preventing hair loss:

| | |
| --- | --- |
| Compound of Example 17 | 3.0 g |
| Propylene glycol | 30.0 g |
| Ethyl alcohol | 40.5 g |
| Water | qs 100.0 g |

This lotion is applied to the scalp once or twice a day, at a rate of 1 ml per application.

Thickened lotion for preventing hair loss:

| | |
| --- | --- |
| Compound of Example 2 | 1.0 g |
| Kawain | 2.0 g |
| Hydroxypropylcellulose marketed by Hercules under the trademark Klucel G | 3.5 g |
| Ethyl alcohol | qs 100.0 g |

This thickened lotion is applied to the scalp once or twice a day, at a rate of 1 ml per application.

Niosomal lotion:

| | |
|---|---|
| Chimexane NL ® | 0.475 g |
| Cholesterol | 0.475 g |
| Monosodium stearylglutamate | 0.05 g |
| Compound of Example 1 | 1.0 g |
| Preservatives | qs |
| Dyes | qs |
| Fragrance | qs |
| Demineralized water | qs 100.0 g |

This lotion is applied to the scalp once or twice a day, at a rate of 1 ml per application.

Lotion for preventing hair loss:

| | |
|---|---|
| Compound of Example 3 | 1.0 g |
| Propylene glycol monomethyl ether marketed under the trademark Dowanol PM by Dow Chemical | 20.0 g |
| Hydroxypropylcellulose marketed by Hercules under the trademark Klucel G | 3.0 g |
| Ethyl alcohol | 40.0 g |
| Water | qs 100.0 g |

This thickened lotion is applied to the scalp once or twice a day, at a rate of 1 ml per application.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A hair growth-/hair loss-affecting cosmetic/therapeutic composition of matter, comprising an effective hair growth stimulating and/or hair loss retarding amount of at least one compound having the structural formula (I):

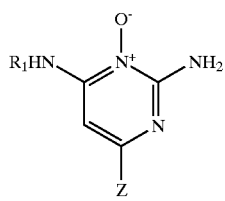

in which $R_1$ is an alkyl radical having from 5 to 20 carbon atoms, and Z is a radical $-OR_2$, wherein $R_2$ is an alkyl radical having from 1 to 12 carbon atoms, or an acid addition salt thereof, formulated into a physiologically acceptable vehicle, diluent or carrier therefor.

2. The cosmetic/therapeutic composition as defined by claim 1, wherein, in formula (I), $R_1$ is an alkyl radical having from 6 to 12 carbon atoms.

3. The cosmetic/therapeutic composition as defined by claim 1, wherein said at least one compound is selected from the group consisting of:

2-amino-4-pentylamino-6-methoxypyrimidine 3-oxide;
2-amino-4-hexylamino-6-methoxypyrimidine 3-oxide;
2-amino-4-heptylamino-6-methoxypyrimidine 3-oxide;
2-amino-4-octylamino-6-methoxypyrimidine 3-oxide;
2-amino-4-nonylamino-6-methoxypyrimidine 3-oxide;
2-amino-4-decylamino-6-methoxypyrimidine 3-oxide;
2-amino-4-undecylamino-6-methoxypyrimidine 3-oxide;
2-amino-4-dodecylamino-6-methoxypyrimidine 3-oxide;
2-amino-4-tridecylamino-6-methoxypyrimidine 3-oxide;
2-amino-4-tetradecylamino-6-methoxypyrimidine 3-oxide;
2-amino-4-pentadecylamino-6-methoxypyrimidine 3-oxide;
2-amino-4-hexadecylamino-6-methoxypyrimidine 3-oxide;
2-amino-4-heptadecylamino-6-methoxypyrimidine 3-oxide;
2-amino-4-octadecylamino-6-methoxypyrimidine 3-oxide;
2-amino-4-nonadecylamino-6-methoxypyrimidine 3-oxide;
2-amino-4-eicosadecylamino-6-methoxypyrimidine 3-oxide;
2-amino-4-pentylamino-6-ethoxypyrimidine 3-oxide;
2-amino-4-hexylamino-6-ethoxypyrimidine 3-oxide;
2-amino-4-heptylamino-6-ethoxypyrimidine 3-oxide;
2-amino-4-octylamino-6-ethoxypyrimidine 3-oxide;
2-amino-4-nonylamino-6-ethoxypyrimidine 3-oxide;
2-amino-4-decylamino-6-ethoxypyrimidine 3-oxide;
2-amino-4-undecylamino-6-ethoxypyrimidine 3-oxide;
2-amino-4-dodecylamino-6-ethoxypyrimidine 3-oxide;
2-amino-4-tridecylamino-6-ethoxypyrimidine 3-oxide;
2-amino-4-tetradecylamino-6-ethoxypyrimidine 3-oxide;
2-amino-4-pentadecylamino-6-ethoxypyrimidine 3-oxide;
2-amino-4-hexadecylamino-6-ethoxypyrimidine 3-oxide;
2-amino-4-heptadecylamino-6-ethoxypyrimidine 3-oxide;
2-amino-4-octadecylamino-6-ethoxypyrimidine 3-oxide;
2-amino-4-nonadecylamino-6-ethoxypyrimidine 3-oxide;
2-amino-4-eicosadecylamino-6-ethoxypyrimidine 3-oxide;
2-amino-4-pentylamino-6-propyloxypyrimidine 3-oxide;
2-amino-4-hexylamino-6-propyloxypyrimidine 3-oxide;
2-amino-4-heptylamino-6-propyloxypyrimidine 3-oxide;
2-amino-4-octylamino-6-propyloxypyrimidine 3-oxide;
2-amino-4-nonylamino-6-propyloxypyrimidine 3-oxide;
2-amino-4-decylamino-6-propyloxypyrimidine 3-oxide;
2-amino-4-undecylamino-6-propyloxypyrimidine 3-oxide;
2-amino-4-dodecylamino-6-propyloxypyrimidine 3-oxide;
2-amino-4-tridecylamino-6-propyloxypyrimidine 3-oxide;
2-amino-4-tetradecylamino-6-propyloxypyrimidine 3-oxide;
2-amino-4-pentadecylamino-6-propyloxypyrimidine 3-oxide;
2-amino-4-hexadecylamino-6-propyloxypyrimidine 3-oxide;
2-amino-4-heptadecylamino-6-propyloxypyrimidine 3-oxide;
2-amino-4-octadecylamino-6-propyloxypyrimidine 3-oxide;

2-amino-4-nonadecylamino-6-propyloxypyrimidine 3-oxide;
2-amino-4-eicosadecylamino-6-propyloxypyrimidine 3-oxide;
2-amino-4-pentylamino-6-butyloxypyrimidine 3-oxide;
2-amino-4-hexylamino-6-butyloxypyrimidine 3-oxide;
2-amino-4-heptylamino-6-butyloxypyrimidine 3-oxide;
2-amino-4-octylamino-6-butyloxypyrimidine 3-oxide;
2-amino-4-nonylamino-6-butyloxypyrimidine 3-oxide;
2-amino-4-decylamino-6-butyloxypyrimidine 3-oxide;
2-amino-4-undecylamino-6-butyloxypyrimidine 3-oxide;
2-amino-4-dodecylamino-6-butyloxypyrimidine 3-oxide;
2-amino-4-tridecylamino-6-butyloxypyrimidine 3-oxide;
2-amino-4-tetradecylamino-6-butyloxypyrimidine 3-oxide;
2-amino-4-pentadecylamino-6-butyloxypyrimidine 3-oxide;
2-amino-4-hexadecylamino-6-butyloxypyrimidine 3-oxide;
2-amino-4-heptadecylamino-6-butyloxypyrimidine 3-oxide;
2-amino-4-octadecylamino-6-butyloxypyrimidine 3-oxide;
2-amino-4-nonadecylamino-6-butyloxypyrimidine 3-oxide;
2-amino-4-eicosadecylamino-6-butyloxypyrimidine 3-oxide; and the branched isomers thereof.

4. The cosmetic/therapeutic composition as defined by claim 1, wherein said at least one compound is 2-amino-4-octylamino-6-butyloxypyrimidine 3-oxide.

5. The cosmetic/therapeutic composition as defined by claim 1, comprising from 0.001% to 10% by weight of said at least one compound.

6. The cosmetic/therapeutic composition as defined by claim 5, comprising from 0.01% to 2% by weight of said at least one compound.

7. The cosmetic/therapeutic composition as defined by claim 1, further comprising an effective amount of at least one antibacterial agent, antiparasitic agent, antifungal agent, antiviral agent, anti-inflammatory agent, antipruriginous agent, anaesthetic, keratolytic agent, anti-free-radical agent, antiseborrhoeic agent, antidandruff agent, antiacne agent or agent for reducing skin differentiation or proliferation or pigmentation, extract of plant, marine or bacterial origin, or mixture thereof.

8. The cosmetic/therapeutic composition as defined by claim 7, comprising an effective amount of at least one imidazole antifungal agent.

9. The cosmetic/therapeutic composition as defined by claim 8, comprising an effective amount of the imidazole antifungal agent ketoconazole.

10. The cosmetic/therapeutic composition as defined by claim 1, formulated for topical application.

11. The cosmetic/therapeutic composition as defined by claim 1, formulated for oral administration.

12. The cosmetic/therapeutic composition as defined by claim 1, formulated for systemic administration.

13. The cosmetic/therapeutic composition as defined by claim 1, further comprising at least one hydrophilic or lipophilic gelling agent, hydrophilic or lipophilic active agent, preservative, antioxidant, solvent, fragrance, filler, sunscreen, odor absorber, dyestuff, colorant or mixture thereof.

14. The cosmetic/therapeutic composition as defined by claim 1, formulated as an aqueous or oily solution, dispersion, lotion, serum, syrup, ointment, emulsion, suspension, cream, gel, mousse, spray, soap or bar.

15. The cosmetic/therapeutic composition as defined by claim 1, formulated as microcapsules, microparticles, a vesicle dispersion, capsules, granules or tablets.

16. The cosmetic/therapeutic composition as defined by claim 1, formulated as a shampoo, hairsetting lotion, hair-styling cream or gel hair-restructuring lotion or permanent-wave formulation.

17. A method for inducing or stimulating the growth of hair or limiting the loss of hair on an individual subject in need of such treatment, comprising administering to said subject, for such period of time as required to elicit the desired response, an effective hair growth stimulating or hair loss retarding amount of at least one compound having the structural formula (I):

$$\text{(I)}$$

in which $R_1$ is an alkyl radical having from 5 to 20 carbon atoms, and Z is a radical $-OR_2$, wherein $R_2$ is an alkyl radical having from 1 to 12 carbon atoms, or an acid addition salt thereof, or of a cosmetic/therapeutic composition comprising said effective amount of said at least one compound, formulated into a physiologically acceptable vehicle, diluent or carrier therefor.

18. The method as defined by claim 17, comprising topically applying said at least one compound or said composition comprising said at least one compound, in said effective amount, onto the head and/or hair of said subject.

* * * * *